United States Patent [19]

Reger et al.

[11] Patent Number: 5,296,193

[45] Date of Patent: Mar. 22, 1994

[54] COMBINED TITRATION APPARATUS

[75] Inventors: Hubert Reger, Tübingen-Pfrondorf; Günther Zimmermann, Filderstadt, both of Fed. Rep. of Germany

[73] Assignee: Deutsche Metrohm Gesellschaft mit beschrankter Haftung & Co. elektronische Messgeräte, Filderstadt, Fed. Rep. of Germany

[21] Appl. No.: 95,120

[22] Filed: Jul. 20, 1993

[30] Foreign Application Priority Data

Apr. 7, 1993 [EP]  European Pat. Off. ........ 93105733.5

[51] Int. Cl.$^5$ ............................................. C01N 27/49
[52] U.S. Cl. ........................................ 422/75; 422/76; 422/82.02; 422/82.03; 204/400; 204/405
[58] Field of Search ............. 422/75, 76, 82.01, 82.02, 422/82.03; 204/400, 405–407; 436/51, 149, 150, 151

[56] References Cited

U.S. PATENT DOCUMENTS 4,244,800  1/1981  Frazzini et al. ................ 204/195 R
5,149,629  9/1992  Rishpon et al. ...................... 435/7.9

Primary Examiner—James C. Housel
Assistant Examiner—David Redding
Attorney, Agent, or Firm—Anderson Kill Olick & Oshinsky

[57] ABSTRACT

A titration apparatus, which operated volumetrically and/or coulometrically, includes a basic apparatus with a control and actuation arrangement for the volumetric metering of reagents, a metering unit for the volumetric titration removably attached to the basic apparatus, and mechanical coupling elements for connecting the metering unit to the actuation device. Instead of the volumetric unit or in addition thereto, a coulometric titration cell may be connected with the basic apparatus directly or by an adapter unit, while using the same control device as the metering unit.

14 Claims, 4 Drawing Sheets

COMBINED TITRATION APPARATUS

BACKGROUND OF THE INVENTION

The invention relates to a volumetrically and/or coulometrically operating titration apparatus. Titration apparatuses can be utilized in the most diverse areas for the chemical identification of one or several substances in specimens. In general chemistry, petrochemistry, in the foodstuff industry, pharmacology and medicine as well as in the water and waste water treatment sector, etc., the amount of a particular substance can be determined by titration. For this purpose, there occurs a precise metering of a reagent with a known content of an active substance, which reacts in a known relationship with the particular substance. The amount of the reagent required up to a specific end point, which is usually recognized with an indicator electrode, is a measure of the amount of the substance to be identified. The feeding of the specific reagent can be accomplished in two different ways, either volumetrically or coulometrically. In the volumetric method, the reagent is supplied to the titration vessel as an admeasured volume by a very precisely controllable piston/cylinder unit (metering unit). In the coulometric method, the reagent is generated electrolytically in a titration vessel. For this purpose, generator-electrodes are used which penetrate the content of the titration vessel. By means of an accurately measured current applied to the electrodes, the reagent is produced in a predetermined amount electrochemically in the titration vessel, which amount then reacts with the particular substance. The current-time period-area is a measure for the amount of the added reagent and thus of the substance to be determined.

As it has already been mentioned, the known titration apparatuses work either according to the volumetric or the coulometric method, meaning if a change of method is to occur it is necessary to use the other appropriate type of a titration apparatus. The procurement of both instruments results in high expenses.

Furthermore, a titration apparatus is known by means of which an associated coulometric titration cell can be operated. In addition, an associated instrument can be allocated which operates according to the volumetric method.

Accordingly, the main object of the invention is a titration apparatus, which can be utilized in a particularly versatile manner and can be purchased and utilized in a cost effective manner. Another object of the invention is a versatile titration apparatus having a simple construction.

SUMMARY OF THE INVENTION

This and other objects of the invention which will become apparent hereinafter are achieved by providing a titration apparatus comprising a control- and actuation device for the volumetric addition of a reagent, a metering unit removably fastened to a basic apparatus for a volumetric titration and mechanical coupling elements for attaching the metering unit to the actuation device. According to another aspect of the present invention, instead of the volumetric metering unit or in addition to the volumetric metering unit, a coulometric titration cell may be directly or by means of an adapter unit attached to the basic apparatus, while using the same control and actuation device. With this configuration, there is provided a coulometric metering unit, together with the advantage that the basic apparatus comprises all components necessary for a volumetric titration. In particular, the control and actuation device for the volumetric metering of the reagent is already present in the basic apparatus. Additional components such as, for instance, the above-mentioned actuation device for the piston/cylinder unit need not be separately allocated to the inventive titration apparatus, as is the case in the present state of the art. The existing basic apparatus according to the invention provides a complete solution for meeting tightest space requirement, while being also suitable for coulometric measurement. At that, the same control device of the basic apparatus is utilized for the current supply for the coulometric method, while also controlling the actuation device of the piston/cylinder unit when a volumetric measurement takes place. It is not required that the coulometric adapter unit must be attached precisely at the same spot on the basic apparatus, at which also the volumetric metering unit can be attached, rather the coulometric adapter unit/metering unit can be attached detachably at another point of the basic apparatus. Alternately or in addition, there can also exist the possibility, that the coulometric adapter unit is not disposed at the basic apparatus itself, rather it is designed as an attachable device, for instance, integrated into a stirrer for stirring the contents of the titration vessel. The attachable device can be connected to an appropriate interface arrangement in the basic apparatus. It is possible furthermore to integrate the coulometric metering unit into the basic apparatus. Because of the possibility resulting from appropriate design, of being able to install and remove the coulometric metering unit at or from the basic apparatus and not only the volumetric metering unit, the coulometric metering unit is also configured as a replacement unit. With this, coulometric and volumetric replacement units can be easily exchanged in a simple manner for the respective utilization purposes. The replacement or exchange units permit a change of a metering unit which, for instance, can differ as far as their maximum reagent amount is concerned.

As it has already been mentioned, it is also possible to design the volumetric metering unit and the coulometric metering unit as exchangeable or replaceable units, wherein the basic apparatus includes a receptacle for the volumetric metering unit, to which also the coulometric adapter unit/metering unit can be detachably attached. This design is particularly practical and expedient. Depending upon the utilization area, a volumetric metering unit or a coulometric adapter unit is selected and preferably snapped into the basic apparatus. If subsequently a determination according to the other measuring methods (for instance, previously volumetric and now coulometric) is to occur, then the volumetric metering unit can merely be replaced with the coulometric adapter unit, with effortless ease.

The basic apparatus comprises connection means for mechanical and/or electrical connection which, upon mounting of the volumetric metering unit and/or the coulometric adapter unit, are connected, preferably automatically, with matching connection elements of the appropriate titration unit(s), metering and/or adapter unit(s). It is sufficient, with the automatic coupling of the connectors of the basic apparatus with matching connectors of the attachable units, to merely attach the desired unit to the basic apparatus. Further manipulations are then not required for this purpose.

As it has already been stated, nearly all building blocks as well as the software used for the basic apparatus, which is computer-controlled, can be utilized for the volumetric as well as the coulometric measuring method. Preferably the metering control unit generates electric control pulses for the feeding of reagent, which control pulses serve for the actuation of the actuation device for the volumetric metering unit (piston/cylinder unit) as well as for actuation of the coulometric adapter unit/metering unit.

According to a preferred embodiment of the invention, the control pulses operate a current generator in the coulometric adapter unit, and the coulometric adapter unit comprises an interface arrangement for connecting electric connectors to the coulometric titration cell. The current generator supplies the current fed to the electrodes located in the coulometric titration cell. The current generator can alternately be located in the basic apparatus.

In another embodiment of the invention, as already has been stated, the current generator for the coulometric metering unit/titration unit is disposed in the basic apparatus, with the basic apparatus comprising an interface arrangement for connecting the electrical connections to the coulometric titration cell. By disposing the current in the basic apparatus, there is provided, among other things, the advantage, that both titration cells can be used for the volumetric and coulometric measurement. The space requirement for this is very small.

According to another preferred embodiment of the invention, the volumetric metering unit for the reagent metering comprises the mentioned piston/cylinder unit, whose piston is actuated by an actuation device. This actuation device is located in the basic apparatus. It is automatically coupled with the piston/cylinder unit upon mounting of the volumetric metering unit. Mechanical coupling elements are provided to this end, which form the mentioned connection means. The number of the generated control pulses of the control device or the integral of the pulse information (current duration) represents a measure for the supplied quantity of a reagent and, thereby, for the substances to be identified or measured. In the volumetric method, this corresponds to the supply of the appropriate amount of the reagent by actuating the piston/cylinder unit. In the coulometric method, the required quantity of the reagent is produced electrolytically by the current triggered by the control pulses.

BRIEF DESCRIPTION OF THE DRAWING

The objects and features of the present invention will become apparent and the invention itself will be best understood from the following detailed description of the preferred embodiments when read with reference to the accompanying drawings, wherein.

DETAILED DESCRIPTION OF THE PREFERRED EMBODIMENTS

Figure 1:
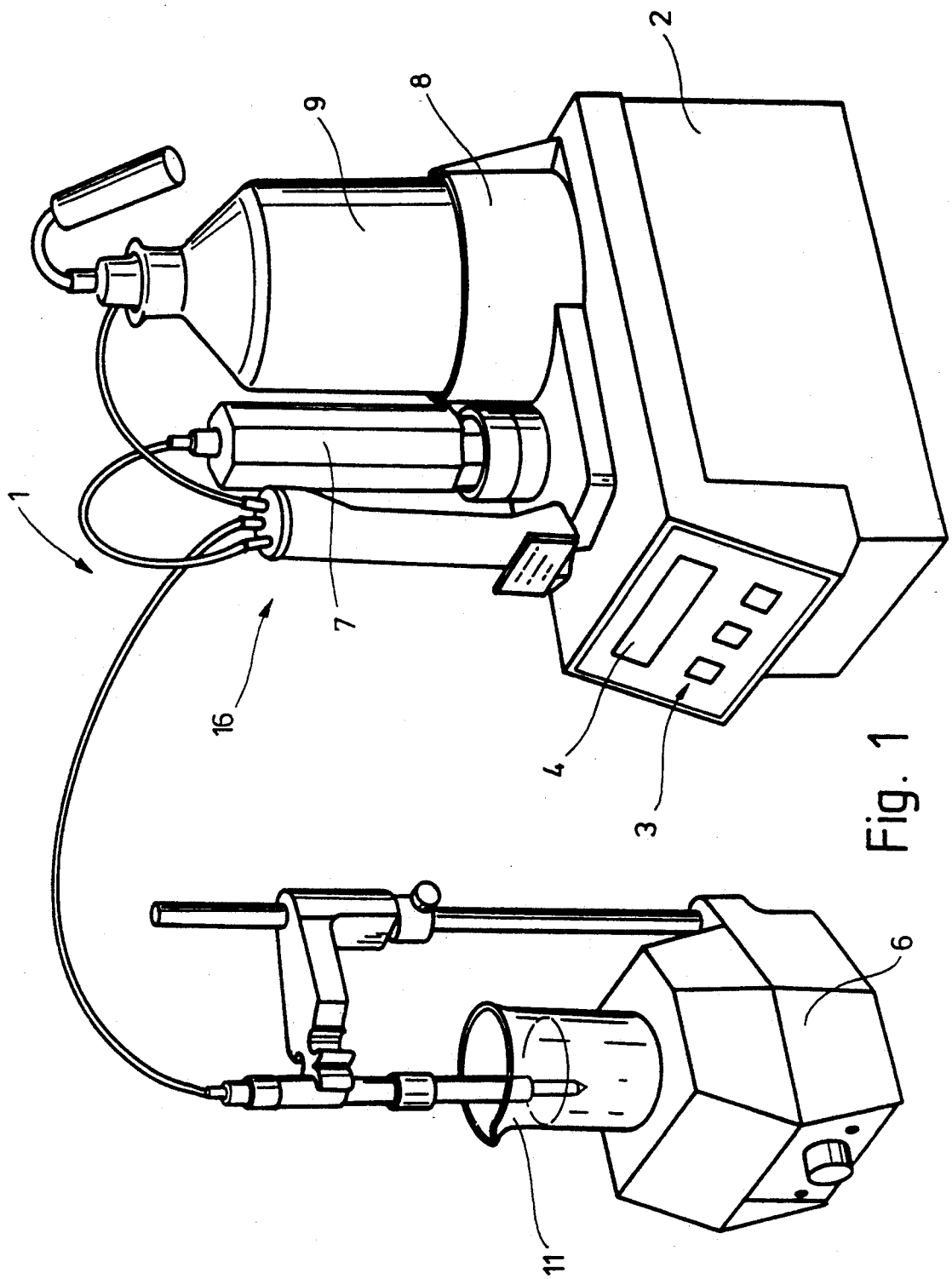
FIG. 1 shows a perspective view of a titration apparatus according to the present invention, on whose basic apparatus a volumetric metering unit is located, and of an associated titration vessel.
Figure 5:
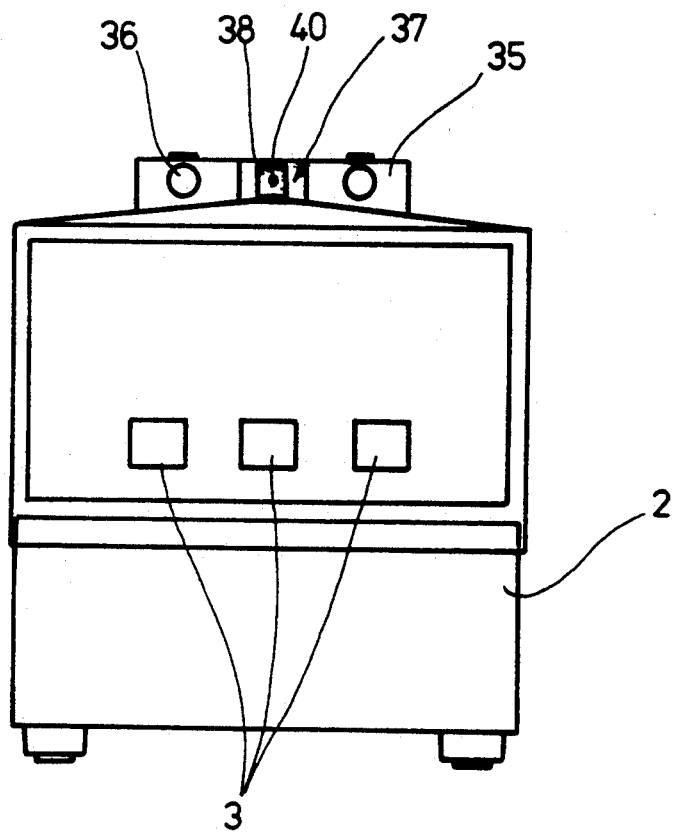
FIG. 5 shows a front view of the basic apparatus.

According to FIG. 1, a titration apparatus 1 comprises a basic apparatus 2 including control elements 3 and a display 4. Control is also possible from an external keyboard (not shown). A control device 22 and an actuation device 21, which serve for the volumetrically controlled addition of a reagent for the purpose of identifying a chemical substance, are located inside of the basic apparatus. The control device 22 and the actuation device 21 are shown schematically in FIG. 5.

A replacement unit, which is configured as a volumetric metering unit 16, is detachably attached to the basic apparatus 2. The attachment can preferably be achieved by placing the volumetric metering unit 16 on the top side of the basic apparatus 2. The top side of the basic apparatus 2 comprises a pedestal 35 forming a receptacle 24 for guidance purposes, upon which pedestal the metering unit 16 having a matching recess is slid on from the front towards the rear and is snapped-in there. Information from the volumetric metering unit 16 is scanned by means of an interfaced arrangement located upon the top side of the basic apparatus. The metering unit 16 has the necessary identification elements required for this purpose at its bottom side. These identification elements can comprise coding magnets, which transmit the maximum metering volume to the basic apparatus 2 (for instance 5 ml, 20 ml, 50 ml). Furthermore, a switch can be provided as an identification element, which is located in a snap-in recess 36 on the pedestal. Furthermore, there is provided a mechanical coupling of a piston/cylinder unit 7 of the volumetric metering unit 16, which serves for the reagent dispensing, with its actuation device 21 located inside of the basic apparatus. This actuation device 21 is designed as a piston drive which drives the piston of the piston/cylinder unit 7 by means of a threaded spindle. The piston drive is actuated by control pulses from the control device 22. Suitable mechanical coupling members 37 are provided for connecting the piston drive to the piston, which are coupled automatically when the metering unit 16 is placed upon the basic apparatus 2. As can be seen from FIGS. 3, 4 and 5, the coupling member 37, which belongs to the basic apparatus 2, consists of a drive shaft end 38 driven by the actuation device 21 and which is stepped down to half the diameter by means of a recess 39. A cross pin 40 is located there. The metering unit 16 has an appropriate matching part, which is provided with a hole for receiving the cross pin 40. The volumetric metering unit 16 has furthermore a receptacle 8 for a container 9 containing the appropriate reagent.

A stirring or agitating arrangement, which is designed as a separate stirrer 6, is located adjacent to the basic apparatus 2. The stirrer 6 and the basic apparatus 2 can be connected with each other by a common base plate (not shown). The titration container 11 with a specimen to be examined is deposited upon the stirrer 6. The reagent is supplied by a suitable hose line. A magnetic agitating or stirring element is located inside the titration container 11, which can be driven by the stirrer 6 through a magnetic coupling.

Preferably different volumetric metering units, which differ in the measured amount of reagents and/or in the type of the reagent container inserted into the receptacle 8, can be successively connected to the basic apparatus 2. Depending upon the utilization purpose, a desired volumetric metering unit 16 is selected from a set of replacement units and is attached to the basic apparatus 2.

Figure 2:
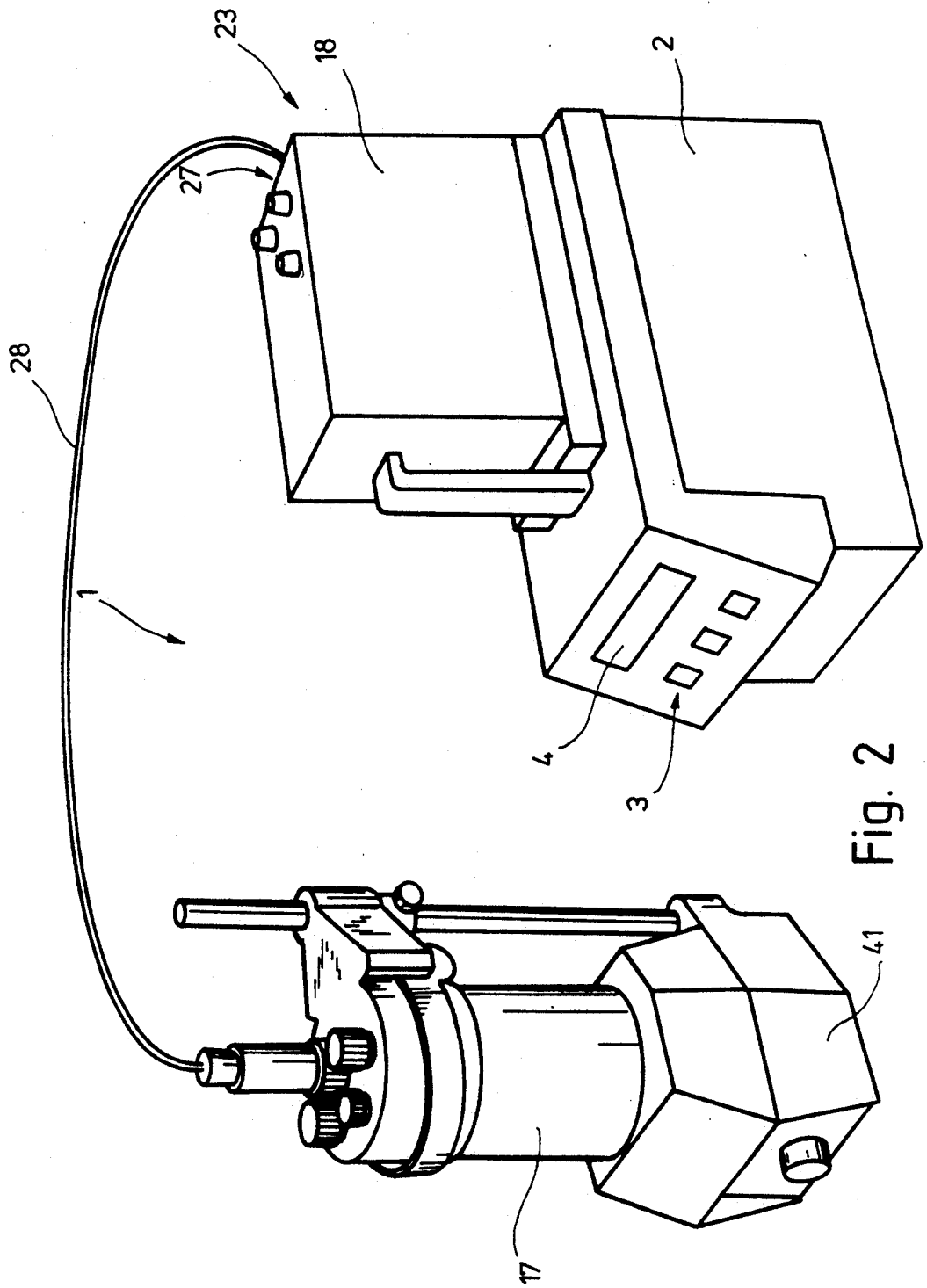
FIG. 2 shows a perspective view of the basic apparatus in FIG. 1 with a coulometric adapter unit placed thereon, and an associated titration cell.
Figure 3:
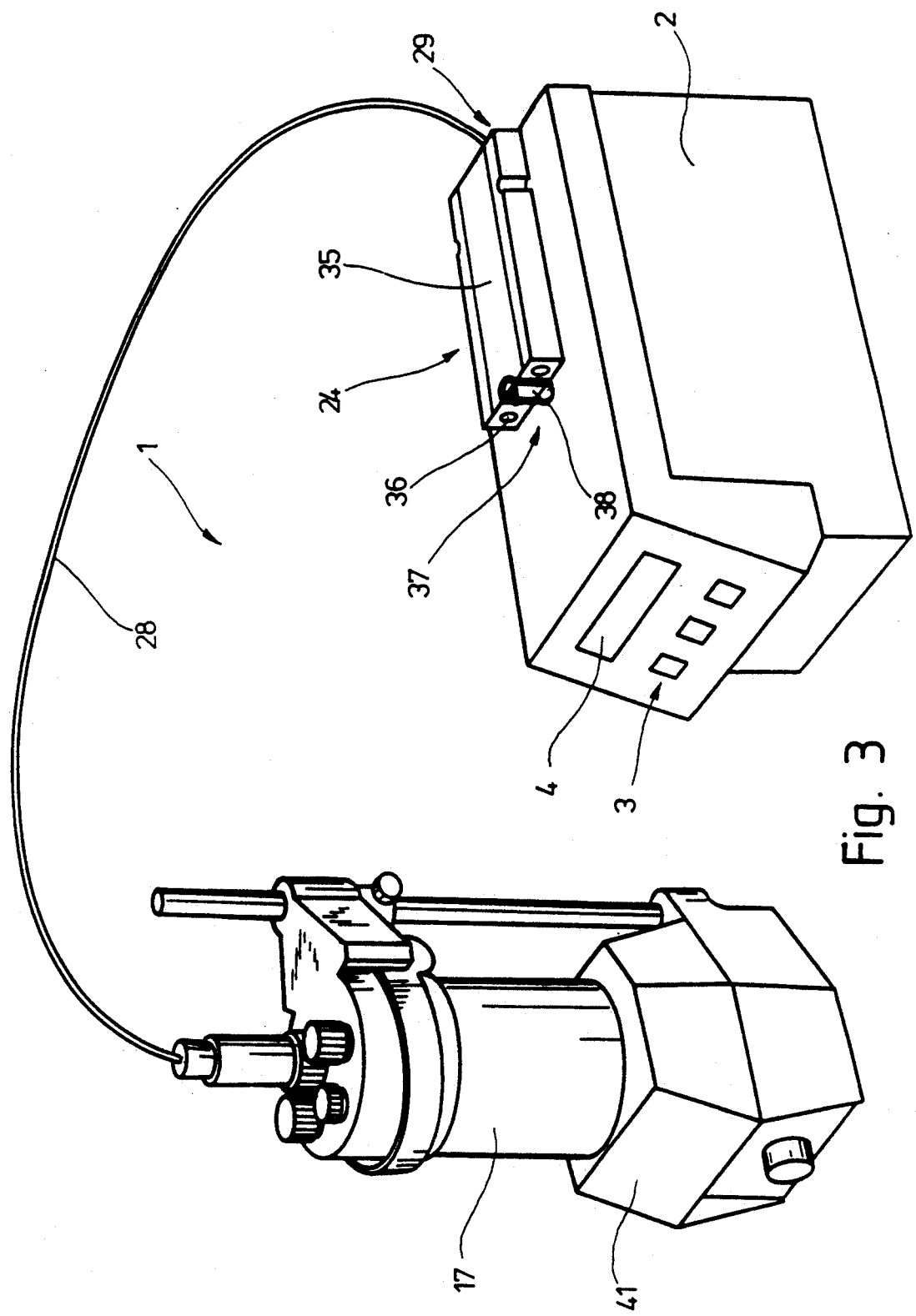
FIG. 3 shows a perspective view of the basic apparatus with integrated coulometric arrangement, as well as the associated coulometric titration cell.
Figure 4:
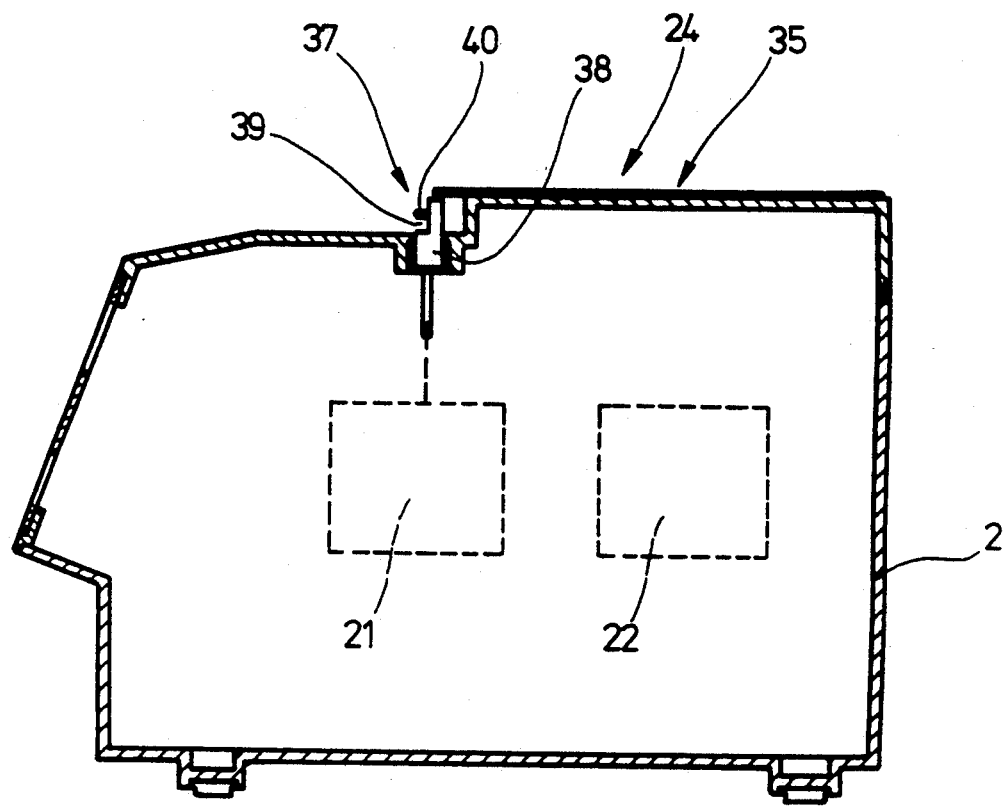
FIG. 4 shows a longitudinal schematic cross-sectional view of the basic apparatus.

In the embodiment shown in FIG. 2, a coulometric adapter unit 18, instead of the volumetric metering unit 16, of the embodiment of FIG. 3, is detachably attached on the basic apparatus 2. This adapter unit 18 is also configured as a replacement unit 23. The coulometric metering unit 18 has an interface 27 from which electric connection lines 28 lead to generator electrodes located inside a titration cell 17. When placing and securing the coulometric adapter unit 18 upon the basic apparatus 2, the required interconnections are produced automatically by means of suitable interface elements (matching electrical connections). In addition, the electrical connections can be established by cables which can be connected by means of soldered connectors on the rear side of the basic apparatus 2 as well as on the coulometric adapter unit 18. The control device 22, which in the embodiment of FIG. 1, actuates the drive of the piston/cylinder unit 7, serves in the embodiment example in FIG. 2 as for the supply of a reagent in a correct amount, so for feeding its control pulses to a current generator located inside of the adapter unit 18, so that the current generator is actuated. The current from the generator is fed to the electrodes in the titration cell 17 which is located upon stirrer 41.

FIG. 3 shows another embodiment of the titration apparatus 1 according to the invention. No titration unit is slid upon the basic apparatus 2. In distinction from the basic apparatus 2 shown in FIGS. 1 and 2, the arrangement necessary for coulometry is contained in the basic apparatus 2 itself. Thus, for instance the current generator required for generation of the current pulse is located inside of the basic apparatus 2. It is actuated by the control device 22 also located in the basic apparatus 2. The connection (among other things of the generator electrodes) to the coulometric titration cell 17, which is located on the separate stirrer 41, is established by means of suitable connections 28 through an interface device 29, located preferably at the rear face of the basic apparatus 2. Apart from the integrated installations for the coulometric method, the basic apparatus 2 of the embodiment of FIG. 3, is very similar to the basic apparatus which was already been described with reference 16 to the FIG. 1. This means that the volumetric metering unit 16 can also be placed upon the top side, so that simultaneously or consecutively a coulometric measurement as well as a volumetric measurement is possible. The appropriate coupling element 37 for the piston/cylinder unit is located for this purpose on the top side of the basic apparatus 2.

It is envisaged to make the complete titration cells including stirrer, electrodes and all plug-in connections, available at the same time for the alternate as well as the simultaneous operation of the volumetric and coulometric arrangements. Thereby, rebuilding or replugging work, when the type of metering is changed, is avoided. In addition, it is possible to effect both types of metering in a common cell alternately.

While particular embodiments of the invention have been shown and descried, various modifications thereof will be apparent to those skilled in the art and, therefore, it is not intended that the invention be limited to the disclosed embodiments or to the details thereof, and departures may be made therefrom within the spirit and scope of the invention as defined in the appended claims.

What is claimed is:

1. Volumetrically and coulometrically operating titration apparatus comprising:
   a basic apparatus including control and actuation means for volumetrically metering of a reagent and for control of a coulometric filtration;
   a separate volumetric metering unit adapted to be detachably connected with the basic apparatus for effecting volumetric titration, the basic apparatus having mechanical connection elements for connecting the metering unit with an actuation device of the control and actuation means; and
   a separate coulometric titration cell adapted to be detachably connected with the basic apparatus for effecting coulometric titration and controllable by the control and actuation means of the basic apparatus.

2. A titration apparatus according to claim 1, wherein the coulometric titration cell and basic apparatus are mounted on a common base plate.

3. A titration apparatus according to claim 1, further comprising a coulometric adapter unit for connecting the coulometric titration cell with the basic apparatus.

4. A titration apparatus according to claim 1, wherein the coulometric adapter unit is connected with the basic apparatus instead of the volumetric metering unit.

5. A titration apparatus according to claim 1, wherein the coulometric adapter unit is connected with the basic apparatus in addition to the metering unit.

6. A titration apparatus according to claim 3, wherein said coulometric adapter unit is formed as an exchange unit, the titration apparatus further comprising detachable connection conduits for connecting said exchange unit to the basic apparatus.

7. A titration apparatus according to claim 3, wherein the volumetric metering unit and the coulometric adapter unit are formed as replaceable units, the basic apparatus comprising a receptacle for detachably receiving one of the metering or coulometric adapter units.

8. A titration apparatus according to claim 7, wherein the basic apparatus comprises at least one of a mechanical and electrical connection means, the volumetric unit and the coulometric adapter unit having matching connection elements which are automatically connected to the connection means with the connection of the volumetric metering unit or coulometric adapter unit with the basic apparatus.

9. A titration apparatus according to claim 1, wherein the control and actuation means comprises a control device that generates control pulses adapted to control both an operation of the actuation device for the volumetric metering unit and an operation of the coulometric titration cell.

10. A titration apparatus according to claim 9, wherein the coulometric adapter unit comprises a current generator controlled by the control pulses generated by the control device, and electrical interface means associated with the current generator, the titration apparatus including electrical conduit means for connecting the electrical interface means with the coulometric titration cell.

11. A titration apparatus according to claim 9, wherein the basic apparatus further comprises a current generator, interface arrangement means, and electrical conduit means for connecting the interface arrangement means with the coulometric titration cell.

12. A titration apparatus according to claim 9, wherein the volumetric metering unit comprises a piston/cylinder unit, the basic apparatus including a piston drive connectable with the piston/cylinder unit and controllable by the control pulses generated by the control device.

13. A titration apparatus according to claim 3, wherein the coulometric adapter unit is formed as a separate unit connectable with the basic apparatus.

14. A titration apparatus according to claim 3, further comprising stirrer means, the coulometric adapter unit being integrated in the stirrer means.

* * * * *